United States Patent [19]

Blechschmitt et al.

[11] 4,036,783

[45] July 19, 1977

[54] SUPPORTED CATALYST CONTAINING VANADIUM AND TITANIUM

[75] Inventors: Kurt Blechschmitt, Schifferstadt; Peter Reuter, Bad Duerkheim; Friedrich Wirth, Ludwigshafen; Gert Buerger, Mannheim; Rolf Seubert, Frankenthal, all of Germany

[73] Assignee: BASF Aktiengesellschaft, Ludwigshafen (Rhine), Germany

[21] Appl. No.: 661,241

[22] Filed: Feb. 25, 1976

[30] Foreign Application Priority Data

Mar. 13, 1975 Germany .......................... 2510994

[51] Int. Cl.$^2$ .................. B01J 21/06; B01J 23/22; B01J 35/02
[52] U.S. Cl. .................................. 252/461; 260/346.4
[58] Field of Search .................... 252/461; 260/346.4

[56] References Cited

U.S. PATENT DOCUMENTS

| 3,565,829 | 2/1971 | Friedrichsen et al. ......... 252/461 X |
| 3,830,755 | 8/1974 | Reuter et al. .................... 252/461 X |

*Primary Examiner*—W. J. Shine
*Attorney, Agent, or Firm*—Keil, Thompson & Shurtleff

[57] ABSTRACT

A supported catalyst containing vanadium and titanium, comprising a ring-shaped carrier having an external diameter of from 7.3 to 8.6 mm, a length of from 5.3 to 7 mm and a wall thickness of from 0.1 to 2 mm, and an active composition, applied thereto, of from 1 to 30 per cent by weight of vanadium pentoxide and from 70 to 99 per cent by weight of titanium dioxide and/or zirconium dioxide.

3 Claims, No Drawings

SUPPORTED CATALYST CONTAINING VANADIUM AND TITANIUM

The present invention relates to a new supported catalyst containing vanadium and titanium, and to its use for the manufacture of phthalic anhydride by catalytic oxidation of o-xylene or napthalene with air.

Supported catalysts containing vanadium and titanium, such as are described, eg., in German Pat. No 1,442,590 or in German Published Application No. 1,642,938, have already been proposed for the manufacture of phthalic anhydride by catalytic oxidation of o-xylene or naphthalene with air. They are manufactured by applying a mixture containing titanium dioxide and a vanadium compound to a carrier which may be, eg., in the form of spheres, pellets, cones or rings, in such amount that, after drying the carrier is coated with from about 0.02 to 2 mm of the active composition of vanadium pentoxide and titanium dioxide. Spherical carriers have proved so successful in respect of the (low) pressure loss in tubular reactors and in respect of the good yield obtained that in industrial installations only spherical catalysts of the said type have found acceptance. Another reason why spherical catalyst carriers are regarded as particularly suitable is that they give good space utilization and little pressure loss in the reaction tube and reduce the risk of incorrect packing when the tubular reactor is filled. As a result of the uniform packing of the catalyst achievable with spherical catalysts, good and uniform heat removal from hot spots and a substantially constant residence time of the gas streams in the catalyst bed are achieved in the highly exothermic oxidation of the hydrocarbons. This in turn permits control of the oxidation reaction, so that over-oxidation can substantially be prevented and products of good quality are obtained in high yields.

It is therefore not surprising that these spherical catalysts are regarded as the optimum technical solution and that whilst further improvement of these catalysts is desirable, these improvements have been sought solely through varying the composition of the catalyst mass.

We have found that a supported catalyst containing vanadium and titanium which comprises an inert, non-porous ring-shaped carrier having an external diameter of from 7.3 to 8.6 mm, a length of from 5.3 to 7.0 mm and a wall thickness of from 0.1 to 2 mm and a layer from 0.05 to 1 mm thick of an active composition comprising from 1 to 30 percent of vanadium pentoxide and from 70 to 99 percent by weight of titanium dioxide and/or zirconium dioxide, applied to the carrier, is particularly suitable for the oxidation of o-xylene or naphthalene with air.

For example, in the manufacture of phthalic anhydride from o-xylene or naphthalene this new catalyst provides surprising advantages in respect of the yield, the life of the catalyst, and the technical details of the oxidation reaction.

The new catalysts comprise, as carriers, ring-shaped carriers having an external diameter of from 7.3 to 8.6 mm, preferably from 7.5 to 8.4 mm, a length of from 5.3 to 7.0 mm, preferably from 5.8 to 6.8 mm, and a wall thickness of from 0.1 to 2 mm, preferably from 0.5 to 1.6 mm and especially from 1.3 to 1.6 mm. These rings consist of inert, non-porous materials, eg. iron, steel, aluminum, porcelain, clay, aluminum oxide or silicates, eg. magnesium silicate, aluminum silicate or zirconium silicate.

The carriers are coated with the catalytic composition by applying a mixture of finely divided titanium dioxide and/or zirconium dioxide and a solution or suspension of a vanadium compound to the carrier. The finely divided titanium dioxide is advantageously anatase having a specific inner surface area of from 5 to 20 $m^2/g$.

Suitable vanadium compounds are vanadium pentoxide or those vanadium compounds which are converted to vanadium pentoxide at elevated temperatures, eg., vanadyl oxalate, vanadyl formate, vanadyl tartrate or ammonium vanadate. Coprecipitates of titanium dioxide and vanadium pentoxide, or titanium-vanadium compounds, eg. titanium vanadates, may also be employed. The mixture to be applied to the carrier is prepared by conventional methods, eg. by mixing the finely divided titanium dioxide and/or zirconium dioxide with a solution or suspension of the vanadium compound in water and/or an organic solvent, eg. formamide or ethanolamine.

The coating itself is advantageously carried out by applying the mixture containing the catalysts to the carrier which is heated to, eg., from 110° to 500° C. The active composition accounts for, eg., from 4 to 30 percent by weight of the finished catalyst. The thickness of the layer of active composition is preferably from 0.05 to 0.5 mm.

The mixture containing the catalytic substances is so chosen that, after drying, the active composition applied to the carrier contains from 1 to 30, preferably from 1 to 15, percent by weight of vanadium pentoxide and from 70 to 99, preferably from 85 to 99, percent by weight of titanium dioxide and/or zirconium dioxide. The catalytic composition may, eg., also contain up to 5% of other compounds, eg. oxides of the elements cesium, rubidium, thallium, phosphorus or antimony. In such cases, appropriate amounts of the said oxides, or of compounds which are converted to these oxides during the coating process, are added to the mixture to be applied to the carrier.

The catalysts of the invention may be used for the oxidation of aromatic and unsaturated aliphatic hydrocarbons, eg. naphthalene, o-xylene, benzene or n-butenes, to give carboxylic acids or their anhydrides, eg. phthalic acid or maleic acid. They give particularly advantageous results when used for the catalytic oxidation of o-xylene or naphthalene with air, to give phthalic anhydride. This oxidation is advantageously carried out in the conventional manner in tubular reactors cooled with salt baths, the latter being at from 330° to 450° C and preferably from 340° to 400° C. With the new catalysts, it is possible to use throughputs of from 4 to 10 $m^3$(S.T.P.) of air or oxygen-containing carrier gas per hour per tube, the tubes having a diameter of from about 16 to 40 mm and a length of from about 1 to 4 m. The air or the gas may be charged with from 20 to 100 g of o-xylene or naphthalene per $m^3$(S.T.P.).

We have found, surprisingly, that with the new catalysts it is possible to achieve not only lower pressure losses than when using spherical carriers, but also higher yields of phthalic anhydride. In addition, it is surprising that the catalysts of the invention lose their high activity less rapidly and have a longer life than the conventional spherical catalysts.

In comparison with spherical catalysts, a further advantage of the catalysts of the invention was found to be that using the same amount of catalyst composition, applied to the carrier, per unit volume of catalyst, the air can be charged with more than 40 g, and up to 48 g, of o-xylene and/or naphthalene per m³ (S.T.P.) of air without the temperatures in the catalyst bed rising to above 500° C, at which, on the one hand, the catalyst is rapidly damaged whilst, on the other hand, over-oxidation, to maleic anhydride, carbon monoxide and carbon dioxide, lowers the yield of phthalic anhydride. This means that phthalic anhydride can now be manufactured with a considerable saving of energy, since, in industrial use of the conventional supported catalysts, the amount of o-xylene or naphthalene must be restricted to a maximum value of about 40 g (per m³) to avoid these disadvantages, thus requiring a larger amount of compressed air.

Furthermore, the catalysts of the invention can be used with a higher throughput of air, or carrier gas containing oxygen, per liter of catalysts than can the conventional spherical catalysts. Thus, in the oxidation of o-xylene or naphthalene, the supported catalysts of the invention can be run with from 6 to 10 m³(S.T.P.) of air per hour per liter of catalyst, but the conventional spherical catalyst can only be run with 4.5 m³(S.T.P.) of air per hour per liter of catalyst, if phthalic anhydride is to be obtained in good quality and high yield.

EXAMPLE 1

1,000 g of steatite rings having an external diameter of 8 mm, a length of 6 mm and a wall thickness of 1.5 mm are heated at 260° C in a coating drum.

A suspension consisting of 400 g of anatase having an internal surface area of 11.2 m²/g, 73.6 g of vanadyl oxalate (corresponding to 30.1 g of vanadium pentoxide), 500 g of water and 100 g of formamide is sprayed onto the rings at this temperature, until the weight of active composition applied is 12.0% of the total weight of catalyst.

The catalytic composition consists of 7.0 percent by weight of vanadium pentoxide and 93.0 percent by weight of titanium oxide. The coating thickness averages 0.13 mm.

A vertical iron tube having an internal diameter of 25 mm and a length of 3 m is filled with 1,150 g of the catalyst prepared above and is surrounded with a salt bath to regulate the temperature. The height of the catalyst packing is 280 cm. Per hour, 188 g of o-xylene mixed with 4,500 l of air are passed at 370° C over this catalyst bed. The pressure loss over the catalyst is 0.33 atmospheres.

The yield is 115 percent by weight of phthalic anhydride, based on 100% pure o-xylene.

EXAMPLE 2

1,000 g of steatite rings having an external diameter of 8 mm, a length of 6 mm and a wall thickness of 1.5 mm are heated at 260° C in a coating drum and are sprayed with the suspension described in Example 1 until the weight of the active composition applied is 8.0% of the total weight of the catalyst.

The catalytic composition consists of 7.0 percent by weight of vanadium pentoxide and 93.0 percent by weight of titanium dioxide. The coating thickness averages 0.09 mm.

A vertical iron tube having an internal diameter of 25 mm and a length of 3 m is filled with 1,130 g of the catalyst prepared above and is surrounded with a salt bath to regulate the temperature. The height of the catalyst packing is 280 cm. Per hour, 160 g of naphthalene with 4,000 l of air are passed at 382° C over this catalyst bed. The pressure loss over the catalyst is 0.28 atmospheres.

The yield is 103.5 percent by weight of phthalic anhydride, based on 100% pure naphthalene.

EXAMPLE 3

1,000 g of steatite rings having an external diameter of 8 mm, a length of 6 mm and a wall thickness of 1.5 mm are heated at 260° C in a coating drum.

A suspension consisting of 400 g of anatase having an internal surface area of 11.2 m²/g, 62.5 g of vanadyl oxalate (corresponding to 25.6 g of vanadium pentoxide), 500 g of water and 100 g of formamide is sprayed onto the rings at this temperature, until the weight of active composition applied is 12.35% of the total weight of catalyst.

The catalytic composition consists of 6.0 percent by weight of $V_2O_5$ and 94.0 percent by weight of $TiO_2$. The coating thickness averages 0.14 mm.

A vertical iron tube having an internal diameter of 25 mm and a length of 3 m is filled with 1,160 g of the catalyst prepared above and is surrounded with a salt bath to regulate the temperature. The height of the catalyst packing is 280 cm. Per hour, 246 g of o-xylene with 6,000 l of air are passed at 380° C over this catalyst bed. The pressure loss over the catalyst is 0.51 atmospheres.

The yield is 114.3 percent by weight of phthalic anhydride, based on 100% pure o-xylene.

EXAMPLE 4

1,000 g of steatite rings having an external diameter of 8 mm, a length of 6 mm and a wall thickness of 1.5 mm are heated at 260° C in a coating drum.

A suspension consisting of 400 g of anatase having an internal surface area of 11.2 m³/g, 73.6 g of vanadyl oxalate (corresponding to 30.1 g of vanadium pentoxide) and 1.16 g of rubidium carbonate in 100 g of water and 100 g of formamide is sprayed onto the rings at this temperature, until the weight of active composition applied is 12.2% of the total weight of catalyst.

The catalytic composition consists of 7.0 percent by weight of $V_2O_5$, 92.73 percent by weight of $TiO_2$ and 0.274 percent by weight of rubidium oxide. The coating thickness averages 0.135 mm.

A vertical iron tube having an internal diameter of 25 mm and a length of 3 m is filled with 1,120 g of the catalyst prepared above and is surrounded with a salt bath to regulate the temperature. The height of the catalyst packing is 280 cm. Per hour, 272 g of o-xylene with 4,000 l of air are passed at 375° C over this catalyst bed. The pressure loss over the catalyst is 0.28 atmospheres.

The yield is 113.5 percent by weight of phthalic anhydride, based on 100% pure o-xylene.

We claim:

1. A supported catalyst comprising an inert, non-porous ring-shaped carrier which has an external diameter of from 7.3 to 8.6 mm, a length of from 5.3 to 7.0 mm and a wall thickness of from 0.1 to 2 mm, and a layer of from 0.05 to 1 mm of an active composition consisting essentially of from 1 to 30 percent by weight of vanadium pentoxide and from 70 to 99 percent by weight of titanium dioxide, applied to the carrier.

2. A supported catalyst as claimed in claim 1, wherein the ring-shaped carrier has an external diameter of from 7.5 to 8.4 mm, a length of from 5.8 to 6.8 mm and a wall thickness of from 0.5 to 1.6 mm.

3. A supported catalyst as claimed in claim 1 wherein said active composition consists essentially of from 1 to 15% by weight of vanadium pentoxide and 85 to 99% by weight of titanium dioxide.

* * * * *